| United States Patent [19] | [11] Patent Number: 4,594,412 |
| Kitagawa | [45] Date of Patent: Jun. 10, 1986 |

[54] METHOD OF ISOLATING SOYASAPONINS

[75] Inventor: Isao Kitagawa, Toyonaka, Japan

[73] Assignee: Osaka Chemical Laboratory Co., Ltd., Osaka, Japan

[21] Appl. No.: 568,714

[22] Filed: Jan. 6, 1984

[30] Foreign Application Priority Data

Mar. 23, 1983 [JP] Japan ................................. 58-49359

[51] Int. Cl.$^4$ .............................................. C07H 1/08
[52] U.S. Cl. ..................................... 536/18.5; 536/5; 536/6.3; 536/128
[58] Field of Search ....................... 536/6.3, 18.5, 128, 536/5

[56] References Cited

U.S. PATENT DOCUMENTS

| 2,566,291 | 8/1951 | Reichstein | 536/5 |
| 3,901,875 | 8/1975 | Park | 536/5 |
| 4,157,894 | 6/1979 | Bombardelli | 536/5 |
| 4,171,430 | 10/1979 | Matsushita et al. | 536/5 |

OTHER PUBLICATIONS

Kitagawa et al., "Chem. Abst.", vol. 84, 1976, p. 132654k.

Nishida et al., "Chem. Abst.", vol. 96, 1982, p. 48165s.

*Primary Examiner*—Johnnie R. Brown
*Attorney, Agent, or Firm*—Stiefel, Gross, Kurland & Pavane

[57] ABSTRACT

A method of isolating soyasaponins which comprises defatting or not defatting the whole plant and/or the seed of a plant belonging to Leguminosae Trifolium, Leguminesae Medicago, Leguminosae Astragalus and Leguminosae Vicia, extracting said whole plant and/or seed with water, an organic solvent miscible with water or a mixture of such organic solvent and water, and isolating soyasaponin I from the extract obtained.

13 Claims, No Drawings

METHOD OF ISOLATING SOYASAPONINS

BACKGROUND OF THE INVENTION

Field of the Invention

The present invention relates to a method of isolating soyasaponin I from the whole part, especially the seed, of plants of Leguminosae except soybean.

Description of the Prior Art

Soyasaponin I is chemically expressed as 3-O-[α-L-rhamnopyranosyl(1→2)-β-D-galactopyranosyl(1→2)-β-D-glucuronopyranosyl]soyasapogenol B of the following structural formula:

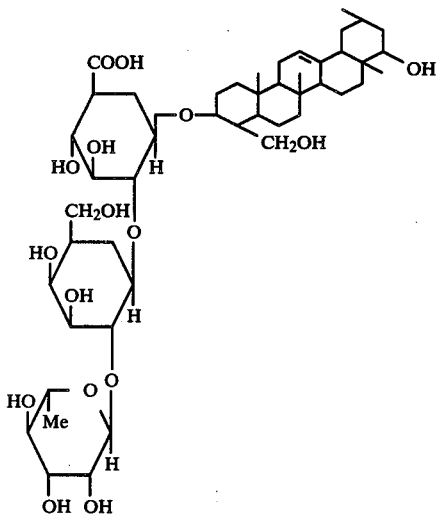

The soyasaponin I is a valuable compound showing metabolic activity (Japanese Patent Laid-open No. 73025/1981), anti-thrombinomimetic activity (Japanese Patent Laid-open No. 95914/1982), etc. in vivo, which is known to be contained in soybean along with soyasaponins II, III, $A_1$ and $A_2$.

Now it has been found after diligent investigation that soyasaponin I is contained in the whole plant, especially in the seed of plants of Leguminosae except soybean, especially plants of Leguminosae Trifolium, Leguminosae Medicago, Leguminosae Astragalus, Leguminosae Vicia, etc. in larger quantities than in soybean.

SUMMARY OF THE INVENTION

The present invention provides a method of isolating soyasaponins characterized by defatting or not defatting the whole plant and/or the seed of a plant belonging to Leguminosae Trifolium, Leguminosae Medicago, Leguminosae Astragalus and Leguminosae Vicia, extracting said whole part and/or seed with water, an organic solvent miscible with water or a mixture of such organic solvent and water, and isolating soyasaponin I from the extract obtained.

According to the method of this invention, a large quantity of soyasaponin I can be obtained easily from the cheap raw material as mentioned above.

DETAILED DESCRIPTION OF THE PREFERRED EMBODIMENTS

Although any plants belonging to the above-mentioned genera of Leguminosae except soybean may be used as the starting material of the method of isolating soyasaponin I of the present invention, the following plants can be mentioned concretely:

(1) L. Trifolium
  *Trifolium pratense Linn.* (red clover)
  *Trifolium repens Linn.* (white clover)
  *Trifolium Lupinaster Linn.*
  *Trifolium hybridum. Linn.*
(2) L. Medicago
  *Medicago sativa Linn.* (alfalfa, lucern)
  *Medicago lupulina Linn.*
  *Medicago denticulata Willd.* (bur clover)
  *Medicago minima Linn.*
(3) L. Astragalus
  *Astragalus sinicus Linn.* (chinese milk vetch)
  *Astragalus refleristipulus Miq.*
(4) L. Vicia
  *Vicia sativa Linn.* (tare).

Although the whole part of the above-mentioned plants may be used as the starting material of the method of this invention, the seed of these plants is preferred and may be used as it is or after it is pulverized.

Besides the above-mentioned plants, plants of *Leguminosae Melilotus* such as *Melilotus suaveolens Ledeb.*, *Leguminosae Crotalaria* such as *Crotalaria sessil ifliflora Linn.*, and *Leguminosae Vicia* such as *Vicia hirsuta Linn.* and *Vicia tetrasperma Linn.* may also be mentioned as the starting material of the method of this invention.

According to the present invention, a method of isolating soyasaponin I from the above-mentioned plants of Leguminosae by defatting or not defatting the whole part and/or the seed of them, extracting said whole part and/or seed with water, an organic solvent miscible with water or a mixture of such organic solvent and water, and isolating the soyasaponin I from the extract obtained, is provided. The invention is concretely explained hereinafter.

The whole part and/or seed as the starting material is used generally in dry state and preferably in pulverized form.

The starting material is not necessarily required to be defatted. However, defatting is preferred, and a rather simple treatment suffices for the defatting, as compared with the case of using soybean as the starting material. The defatting is effected with an ordinary fat-soluble organic solvent such as ether, hexane, benzene, petroleum ether, ligroin, ethyl acetate or the like, usually under heating. Preferable solvents are ethylacetate and hexane. The defatting may be effected after the treatment for extraction, which is described hereinafter.

Next, the starting material defatted or not defatted is extracted with water, an organic solvent miscible with water or a mixture of such organic solvent and water. As the organic solvent miscible with water, there can be mentioned lower aliphatic alcohols, more concretely, methanol, ethanol, propanol, butanol and the like. The extraction is effected with water, a lower aliphatic alcohol as mentioned above or such alcohol containing water, while heating at a temperature where such solvent boils. It is preferable to carry out the extraction with methanol. The treatment for extraction is preferably repeated several times, and the amount of solvent used at one time is preferably about 1 to 5 times (weight/weight) of the material.

Then, the extract is concentrated at as low temperature and under as low pressure as possible. As the concentration proceeds to some degree, brown precipitates can be formed in some cases. In such cases, it is preferable to filter off the precipitates. The filtrate is further concentrated to obtain a concentrated extract.

Isolation of soyasaponin I from the concentrated extract so obtained is performed as described below.

The concentrated extract is dissolved in water or a water containing approximately 30% or less of a lower aliphtic alcohol, and the solution is brought in contact with an adsorbent consisting of a porous, cross-linked polystyrene resin having macro-network structure, for example, Cervachrome XAD-type 2, to adsorb soyasaponins. Then, elution with a lower aliphatic alcohol or a water containing approximately 30% or more of a lower aliphatic alcohol is effected. The eluate obtained is concentrated at as low temperature and under as low pressure as possible. Then, soyasaponin I is isolated from the concentrated liquor by column chromatography on silica gel. As the silica gel for this case, Silica gel 60 (Merck, 70-230 mesh) can be mentioned, and as the eluting solvent there can be mentioned the lower layer of a mixture of chloroform: methanol: water (65:35:10).

Isolation of soyasaponin I from the above-mentioned concentrated extract may be effected also in the following manner:

The concentrated extract is first extracted with n-butanol, by distributing it with a mixture of water and n-butanol. This distributional extraction may be effected (i) by shaking the concentrated extract with a mixture of water and n-butnol in a ratio by weight of approximately 2:1 to approximately 1:2, preferably with that in a ratio by weight of approximately 1:1, (ii) by suspending the concentrated extract in water and then shaking the suspension with n-butanol, or (iii) by dissolving the concentrated extract in n-butanol saturated with water and then shaking the solution with water. Thus the target saponins are transferred into the n-butanol layer. To explain the above case (ii) more particularly, the concentrated extract is suspended in water of approximately same weight and the suspenson is shaken with n-butanol of approximately 1.0 to 2.0 times by weight. By repeating this treatment 2 to 3 times, the target soyasaponins are transferred into the n-butanol layer. The treatment is effected at normal room temperature.

The n-butanol layer thus obtained is concentrated at as low temperature and under as low pressure as possible, to obtain raw soyasaponins. The concentration may be effected until dryness results.

From the raw soyasaponins obtained as above, soyasaponin I is isolated in either of the following ways:

A first method is performed by treating the raw soyasaponins with a combination of a soyasaponin-soluble organic solvent and a soyasaponin-insoluble organic solvent. Soyasaponins are very soluble in methanol, soluble in water, ethanol, dimethyl sulfoxide, pyridine, etc., and much less soluble in ethers, hexane, chloroform, acetone, ethyl acetate, etc. Although any combination of solvents selected from these may be used, the combination of methanol and ethyl ether and the combination of methanol and ethyl acetate are preferred. Thus, soyasaponin I separates out as the raw soyasaponins are dissolved in a soyasaponin-soluble organic solvent and the solution is added to a soyasaponin-insoluble solvent or a soyasaponin-insoluble solvent is added to the solution. It is also possible to dissolve the soyasaponin I so obtained in water or a lower aliphatic alcohol and treat it with activated charcoal. The resulting soyasaponin I may further be recrystallized from a mixed solvent consisting of chloroform: methanol: water.

In a second method, the raw soyasaponins are dissolved in an aqueous lower aliphatic alcohol solution of an alkali hydroxide and then the solution is heated to such degree as it boils. As the alkali hydroxide used in this case, there can be mentioned sodium hydroxide, potassium bydroxide, etc. As the lower aliphatic alcohol, there can be mentioned methanol, ethanol, propanol, etc. and methanol and ethanol are preferred. Next, the resulting solution is neutralized, for example, by passing it through a column of an ion-exchange resin of strong acid type. As the ion-exchange resin of strong acid type used for the neutralization, there can be mentioned ion-exchange resins of Dowex 50 WX series such as Dowex 50 WX 8 and those of Amberlite IR-120 series. The solution thus neutralized is concentrated at as low temperature and under as low pressure as possible. Then, soyasaponin I is isolated from the concentrated liquor by column chromatography on silica gel. As the silica gel for this case, Silica gel 60 (Merck, 70-230 mesh) can be mentioned, and as the eluting solvent the lower layer of a mixture of chloroform: methanol: water (65:35:10) can be mentioned.

Preparation of soyasaponin I according to the method of this invention is illustrated by the following Examples. The invention, however, shall not be limited to these Examples.

EXAMPLE 1

*Medicago sativa Linn.* (alfalfa, commercially available in Osaka, Japan) of Leguminosae Medicago (4.5 Kg) is pulverized and then defatted by heating it in ethyl acetate (9 l) under reflux for 3 hours. To the defatted pulverized seed of alfalfa, methanol (4 l) is added and the mixture is heated under reflux for 5 hours. By filtration, methanol extract is obtained. Methanol (4 l) is newly added to the residue and extraction is effected by heating. The same operation is repeated 5 times in total. The methanol extracts obtained are combined and the solvent is distilled off under reduced pressure to obtain concentrated methanol extract (610 g).

The concentrated methanol extract (610 g) is distributed in a mixture of n-butanol and water (1:1, 2 l). By removing solvent from the n-butanol layer by distillation under reduced pressure, an extract transferred into n-butanol (280 g) is obtained. The extract transferred into n-butanol (140 g) is dissolved in 5% potassium hydroxide/methanol (500 ml) and the solution is heated under reflux for 1 hour. Then, the solution is neutralized with Dowex 50 WX 8 ($H^+$ type) and the solvent is removed by distillation under reduced pressure. From the concentrated liquor, soyasaponin I (24.8 g:0.6% from the seed) is obtained by isolation by column chromatography on silica gel [carrier: Silica gel 60 (Merck, 70-230 mesh), eluting solvent: chloroform: methanol: water (65:35:10, the lower layer)].

EXAMPLE 2

To the same pulverized seed (1 Kg) of *Medicago sativa Linn.* (alfalfa) as the starting material of Example 1, methanol (1 l) is added. The mixture is heated under reflux for 5 hours. By filtration, methanol extract is obtained. Methanol (1 l) is newly added to the residue and extraction is effected by heating. The same operation is repeated 5 times in total. The methanol extracts are combined and then concentrated under reduced pressure (to approximately 1 l). The resulting concentrated methanol extract is extracted with n-hexane (2 l).

By removing solvent from the defatted methanol extract by distillation under reduced pressure, concentrated methanol extract (150 g) is obtained. Then, the concentrated methanol extract (150 g) is distributed in a mixture of n-butanol and water (1:1, 1 l). By removing solvent from the n-butanol layer by distillation under reduced pressure, an extract transferred into n-butanol (70 g) is obtained.

The extract transferred into n-butanol (70 g) is dissolved in methanol (100 ml) and the solution is added dropwise to ethyl acetate (1.5 l) while stirring. The precipitates formed are separated by filtration to obtain raw saponin fraction (7.3 g).

The raw saponin fraction (7.3 g) is dissolved in methanol (200 ml) and the solution is decolorized with activated charcoal ("Seisei Shirasagi"-Takeda Chemical, 20 g). By crystallization from a mixed solvent; chloroform: methanol: water, soyasaponin I (4 g, 0.4%) is obtained.

EXAMPLE 3

The seed of *Trifolium pratense Linn.* of Leguminosae Trifolium (1 Kg) is pulverized and then defatted by heating it in ethyl acetate (3 l) under reflux for 3 hours. To the defatted, pulverized seed is added methanol (1.5 l), and the mixture is heated under reflux for 4 hours. By filtration, methanol extract is obtained. With the residue, the above operation for extraction is repeated 4 times. The methanol extracts obtained are combined and then the solvent is removed by distillation under reduced pressure at a temperature of 60° C. or lower to obtain concentrated methanol extract (140 g). The concentrated methanol extract is distributed in a mixture of n-butanol and water (1:1, 1 l). By removing solvent from the n-butanol layer by distillation under reduced pressure at a temperature of 60° C. or lower, an extract (64 g) is obtained. The extract is dissolved in 5% potassium hydroxide/methanol (300 ml) and the solution is heated under reflux for 1 hour. Then, the solution is neutralized with Dowex 50 WX 8 (H+ type) and the solvent is removed by distillation under reduced pressure at a temperature of 60° C. or lower. From the concentrated liquor, soyasaponin I (4.1 g, yield 0.41%) is obtained by isolation by column chromatography on silica gel [carrier: Silica gel 60 (Merck, 70–230 mesh), eluting solvent: the lower layer of chloroform: methanol: water (65:35:10)].

EXAMPLE 4

The seed of *Trifolium repens Linn.* of Leguminosae Trifolium (1 Kg) is pulverized and then defatted by heating it in n-hexane (3 l) under reflux for 3 hours. The defatted, pulverized seed is extracted in n-butanol saturated with water (10 l) by stirring 3 times on a boiling water bath, each time for 1 hour. The solution obtained is washed 3 times with water saturated with n-butanol (3 l) to remove contaminating sugars and coloring matters by transferring them into water. The n-butanol layer saturated with water is evaporated under reduced pressure at a temperature of 80° C. or lower to dryness. The residue is dissolved in methanol (1 l), and the solution is poured into ether (6 l) while stirring. After leaving to stand for 1 day, raw saponins (6.8 g) which precipitates are separated by filtration. The raw saponins are dissolved in methanol (200 ml) and activated charcoal (20 g) is added to the solution. After stirring for 30 minutes, the mixture is filtered. The filtrate obtained is evaporated to dryness. The residue is further recrystallized from the lower layer of a mixture of chloroform: methanol: water (65:35:10), whereby soyasaponin I (3.9 g, yield 0.39%) is obtained.

EXAMPLE 5

The seed of *Astragalus sinicus Linn.* of Leguminosae Astragalus (1 Kg) is pulverized and then defatted by heating it in n-hexane (3 l) under reflux for 3 hours. Methanol (1.5 l) is added to the defatted seed and the mixture is heated under reflux for 4 hours. By filtration, methanol extract is obtained. The operation as above is repeated 5 times, and the methanol extracts obtained are combined. By removing solvent by distillation under reduced pressure at a temperature of 60° C. or lower, concentrated extract (152 g) is obtained. The concentrated extract is distributed in a mixture of water and n-butanol (1:1, 1 l). By removing solvent from the n-butanol layer by distillation under reduced pressure at a temperature of 60° C. or lower, a residue (48 g) is obtained. The residue is dissolved in 5% potassium hydroxide/methanol (200 ml) and the solution is heated under reflux for 1 hour. Then, the solution is neutralized with Dowex 50 WX 8 (H+ type) and the solvent is removed by distillation under reduced pressure at a temperature of 60° C. or lower. From the concentrated liquor, soyasaponin I (0.9 g, yield 0.09%) is obtained by isolation by column chromatography on silica gel [carrier: silica gel 60 (Merck, 70–230 mesh), eluting solvent: the lower layer of a mixture of chloroform: methanol: water (65:35:10)].

EXAMPLE 6

The seed of *Vicia sativa Linn.* (tare) of Leguminosae Vicia (1 Kg) is defatted by heating it in n-hexane (10 l) under reflux twice, each time for 1 hour. Methanol (3 l) is added to the defatted dry seed and the mixture is heated under reflux for 1 hour. The resulting mixture is filtered. The operation as above is repeated 3 times, and the extracts are combined. The combined extracts are concentrated under reduced pressure at a temperature of 60° C. or lower to dryness. The evaporation residue is dissolved in water (100 ml), and the solution is poured to the top of a column of Cervachrome XAD-type 2, a synthetic resin adsorbent. The column is prepared beforehand by filling Cervachrome XAD-type 2 (0.9 Kg), dispersed in water, into a column having an inside diameter of 4 cm. The solution is made to pass through said column at a flow rate of 20 ml/minute whereby soyasaponins are adsorbed on the resin. Further, water is poured into the column until the water effluent is no longer colored, to remove impurities. Then, 99% methanol (approximately 5 l) is made to pass through the column at a flow rate of 10 ml/minute to elute soyasaponins. Whether the elution has been completed or not is confirmed by means of thin-layer chromatography [carrier: Kieselguhr F 254, solvent: the lower layer of chloroform-methanol-water (65:35:10), detection: spraying with 1% ceric sulfate-10% sulfuric acid, followed by heating for 5 minutes]. The eluate obtained is evaporated at a temperature of 60° C. or lower to dryness. The residue (3.7 g) is dissolved in methanol (200 ml) and the solution is decolorized by stirring it with activated charcoal (20 g) added thereto for 30 minutes. After filtration, the methanol solution is evaporated and the resulting residue is recrystallized from a mixed solvent chloroform-methanol-water to obtain soyasaponin I (1.6 g, yield 0.16%).

EXAMPLE 7

The dry whole plant of *Medicago sativa Linn.* (alfalfa) of Leguminosae Medicago is cut into pieces having the size of approximately 0.5 cm. Ethyl acetate (3 l)is added to the pieces (1 Kg) and the mixture is heated under reflux for 3 hours. To the whole plant of alfalfa thus defatted, methanol (3 l)is added and the mixture is heated under reflux for 3 hours. By filtration, methanol extract is obtained. The operation as above is repeated 3 times, and the extracts are combined. The solvent is removed under reduced pressure at a temperature of 60° C. or lower. The residue is dissolved in water (100 ml), and the solution is poured to the top of a column of Cervachrome XAD-type 2, a synthetic resin adsorbent. Said column is prepared beforehand by filling Cervachrome XAD-type 2, (0.9 Kg), dispersed in water (1.5 l), into a column having an inside diameter of 4 cm. The solution is made to pass through the column at a flow rate of 20 ml/minute whereby soyasaponins are adsorbed on the resin. Further, water is poured to the top of the column until the water effluent is no longer colored, to remove impurities. Then, 99% methanol (approximately 4 l) is poured to the top of the column at a flow rate of 10 ml/minute to elute soyasaponins. Whether the elution has been completed or not is judged by means of the same thin-layer chromatography method as that explained in Example 6. The eluate obtained is evaporated at a temperature of 60° C. or lower to dryness. The residue (1.4 g), is dissolved in methanol (100 ml), and the solution is decolorized by stirring it with activated charcoal (10 g) added thereto for 30 minutes. After filtration, the methanol solution is evaporated and the residue obtained is recrystallized from a mixed solvent chloroform-methanol-water to obtain soyasaponin I (0.8 g, yield 0.08%).

EXAMPLE 8

With respect to the seed and the whole plant of *Trifolium Lupinaster Linn.*, *Trifolium hybridum Linn.*, *Medicago lupulina Linn.*, *Medicago denticulata Wild.*, *Medicago minima Linn.* and *Astragalus refleristipulus Miq.*, the existence of soyasaponin I was confirmed by means of thin-layer chromatography, as described hereinafter.

A sample (1 g) of each material was extracted with methanol (10 ml) by heating for 30 minutes, and a thin-layer plate of silica gel was spotted with the filtrate. The same thin-layer plate was spotted also with 0.01% solution of authentic soyasaponin I. After development with a mixed solvent chloroform-methanol-water (6:4:1), a solution of 1% ceric sulfate-10% sulfuric acid was sprayed. After heating at 105° C. for 5 minutes, the spot of each sample was of the same Rf value and color (reddish violet) as the spot of authentic soyasaponin I.

What is claimed is:

1. A method of isolating soyasponin I which comprises using the whole plant or the seed of a plant belonging to *Medicago sativa Linn.*, *Trifolium pratense Linn.*, *Trifolium repens Linn.*, *Astragalus sinicus Linn.* and *Vicia sativa Linn.*, treating said whole plant or seed with water, an organic solvent miscible with water or a mixture of such organic solvent and water to obtain an extract and isolating soyasaponin I a compound having the formula

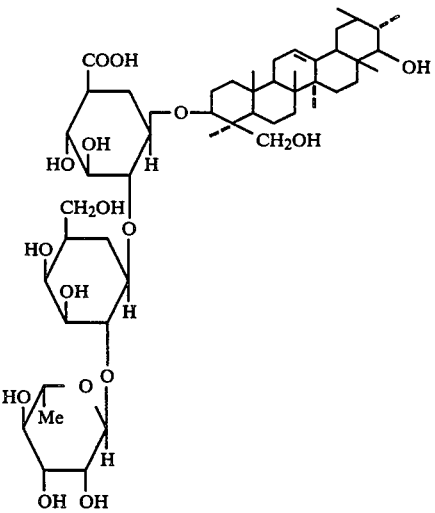

from the obtained extract.

2. A method as claimed in claim 1, wherein the plant is *Medicago sativa Linn.*

3. A method as claimed in claim 1, wherein the organic solvent miscible with water is a lower aliphatic alcohol.

4. A method as claimed in claim 3, wherein the lower aliphatic alcohol is methanol, ethanol, propanol or butanol.

5. A method as claimed in claim 1, wherein, after the extraction, the extract is concentrated, the concentrated extract is dissolved in water or water containing a lower aliphatic alcohol, the solution is brought in contact with an adsorbent consisting of a porous, cross-linked polystyrene resin having macro-network structure to adsorb soyasaponins and then the saponins are eluted with a lower aliphatic alcohol or water containing a lower aliphatic alcohol, the eluate is concentrated, and soyasaponin I is isolated from the concentrated eluate by means of column chromatography.

6. A method as claimed in claim 1, wherein, after the extraction, the extract is concentrated, the concentrated extract is distributed in a mixture of water and n-butanol, the n-butanol extract obtained is concentrated and the resulting raw soyasaponins are dissolved in a lower aliphatic alcohol, and the solution is treated with a soyasaponin I-insoluble organic solvent to isolate soyasaponin I.

7. A method as claimed in claim 1, wherein, after the extraction, the extract is concentrated, the concentrated extract is distributed in a mixture of water and n-butanol, the n-butanol extract so obtained is concentrated and the resulting raw soyasaponins are dissolved in a mixture of a lower aliphatic alcohol and an aqueous solution of an alkali hydroxide, the solution is neutralized with an ion-exchange resin of strong acid type and then concentrated, and soyasaponin I is isolated from the concentrate by means of column chromatography.

8. A method as claimed in claim 5 or 6, wherein the lower aliphatic alcohol is methanol or ethanol.

9. A method as claimed in claim 5 or 7, wherein the column chromatography uses a silica column and as an eluent a mixture of chloroform, methanol and water.

10. A method as claimed in claim 6, wherein the soyasaponin I-insoluble organic solvent is ethyl ether or ethyl acetate.

11. A method as claimed in claim 6, wherein the soyasaponin I which seperates out by treatment with a soyasaponin I-insoluble organic solvent is dissolved in water or lower aliphatic alcohol and the resultant solution is treated with activated carbon.

12. A method as claimed in claim 7, wherein the lower aliphatic alocohol is methanol or ethanol and the alkali hydroxide is sodium hydroxide or potassium hydroxide.

13. The method of any one of claims 1, 3, 4, 5, 6 or 7, wherein said plant or seed of said plant is defatted before treating.

* * * * *